(12) United States Patent
Ehlert et al.

(10) Patent No.: US 11,090,417 B2
(45) Date of Patent: Aug. 17, 2021

(54) SUCTIONING AND SUPPLY DEVICE WITH DRIVE UNIT AND CONNECTING PART

(71) Applicant: MEDELA HOLDING AG, Baar (CH)

(72) Inventors: Hilmar Ehlert, Hergiswil (CH); Lukas Bannwart, Rotkreuz (CH)

(73) Assignee: MEDELA HOLDING AG, Baar (CH)

( * ) Notice: Subject to any disclaimer, the term of this patent is extended or adjusted under 35 U.S.C. 154(b) by 222 days.

(21) Appl. No.: 16/335,143

(22) PCT Filed: Sep. 18, 2017

(86) PCT No.: PCT/EP2017/073464
§ 371 (c)(1),
(2) Date: Mar. 20, 2019

(87) PCT Pub. No.: WO2018/054833
PCT Pub. Date: Mar. 29, 2018

(65) Prior Publication Data
US 2019/0275219 A1    Sep. 12, 2019

(30) Foreign Application Priority Data

Sep. 20, 2016 (EP) ..................................... 16189674

(51) Int. Cl.
*A61M 1/00* (2006.01)
*A61F 9/007* (2006.01)

(52) U.S. Cl.
CPC ....... *A61M 1/0058* (2013.01); *A61F 9/00736* (2013.01); *A61M 1/82* (2021.05);
(Continued)

(58) Field of Classification Search
CPC .............. A61M 1/0058; A61M 1/0088; A61M 1/0072; A61M 2205/12; A61M 2202/08;
(Continued)

(56) References Cited

U.S. PATENT DOCUMENTS 4,634,024 A    1/1987  Vollenweider
6,280,440 B1 * 8/2001  Gocho ............... A61B 18/1492
                                                    604/151
(Continued)

FOREIGN PATENT DOCUMENTS

CN    104771801 A    7/2015
CN    205515735 U    8/2016
(Continued)

OTHER PUBLICATIONS

U.S. Appl. No. 16/333,877, filed Mar. 15, 2019 (as US national phase of PCT/EP2017/073466, international filed Sep. 18, 2017).
(Continued)

*Primary Examiner* — Theodore J Stigell
*Assistant Examiner* — Rachel T. Smith
(74) *Attorney, Agent, or Firm* — Marshall, Gerstein & Borun LLP

(57) ABSTRACT

Provided is a device for suctioning bodily fluids and for supplying a fluid substance to a human or animal body, in which the device includes a drive unit (1, 1', 1"; 2) having a drive (20), a pump head (30, 30', 30") which is drivable by the drive (20) and a connecting part (5, 7', 4") which is releasably connectable to the drive unit (1, 1', 1"; 2) and has a tube guide (555, 710', 43"). The tube guide (555, 710', 43") is realized in such a manner for receiving a tube (I) that the tube, in combination with the pump head (30, 30', 30"), forms a peristaltic pump (3) by way of which the fluid substance is conveyable through the tube (I) to the human or animal body. The pump head (30, 30', 30") is incorporated in the connecting part (5, 7', 4"), and the drive unit (1, 1', 1"; 2) includes a coupling element (24, 24') which is connected to the drive (20) in order to couple the pump head (30, 30', 30") to the drive (20).

14 Claims, 9 Drawing Sheets

(52) U.S. Cl.
CPC .......... *A61M 1/90* (2021.05); *A61B 2217/005* (2013.01); *A61B 2217/007* (2013.01); *A61M 2202/08* (2013.01); *A61M 2205/12* (2013.01)

(58) Field of Classification Search
CPC .......... A61M 2209/086; A61F 9/00736; A61B 2217/005; A61B 2217/007
See application file for complete search history.

(56) References Cited

U.S. PATENT DOCUMENTS

| | | | |
|---|---|---|---|
| 8,591,453 | B2 | 11/2013 | Stubkjaer et al. |
| 2004/0202561 | A1 | 10/2004 | Hershberger et al. |
| 2006/0025727 | A1 | 2/2006 | Boehringer et al. |
| 2008/0154182 | A1 | 6/2008 | Martin et al. |
| 2008/0154184 | A1 | 6/2008 | Blight et al. |
| 2008/0154185 | A1 | 6/2008 | Blight |
| 2010/0174415 | A1* | 7/2010 | Humayun .............. A61B 90/98 700/282 |
| 2012/0302976 | A1 | 11/2012 | Locke et al. |
| 2013/0085462 | A1 | 4/2013 | Nip et al. |
| 2013/0303978 | A1* | 11/2013 | Ross ....................... A61F 9/008 604/30 |
| 2014/0163487 | A1 | 6/2014 | Tout et al. |
| 2016/0015873 | A1 | 1/2016 | Robinson et al. |
| 2016/0095964 | A1 | 4/2016 | Tapadiya |

FOREIGN PATENT DOCUMENTS

| | | |
|---|---|---|
| DE | 202015006341 U1 | 11/2015 |
| EP | 0293081 A1 | 11/1988 |
| EP | 2883555 A2 | 6/2015 |
| FR | 2624376 A1 | 6/1989 |
| FR | 2624377 A1 | 6/1989 |
| FR | 2624378 A1 | 6/1989 |
| FR | 2960423 A1 | 12/2011 |
| WO | WO-98/06446 A2 | 2/1998 |
| WO | WO-2011/018132 A1 | 2/2011 |
| WO | WO-2014/045047 A1 | 3/2014 |
| WO | WO-2015/091070 A1 | 6/2015 |
| WO | WO-2016/065335 A1 | 4/2016 |
| WO | WO-2016054470 A1 | 4/2016 |

OTHER PUBLICATIONS

International Search Report for International Application No. PCT/EP2017/073466, dated Feb. 28, 2018.
International Search Report for International Application No. PCT/EP2017/073464, dated Apr. 9, 2018.

* cited by examiner

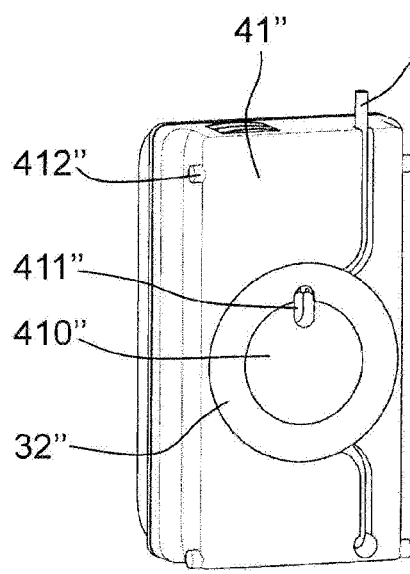
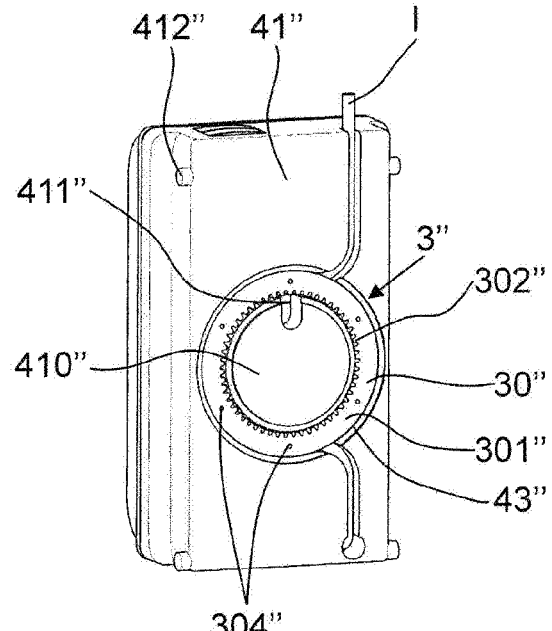
FIG. 20    FIG. 21
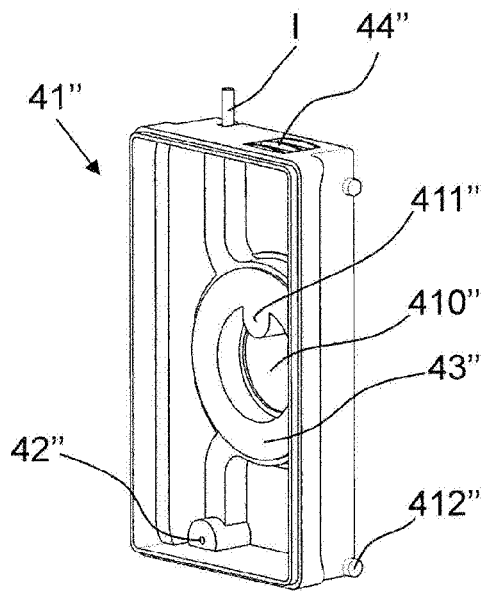
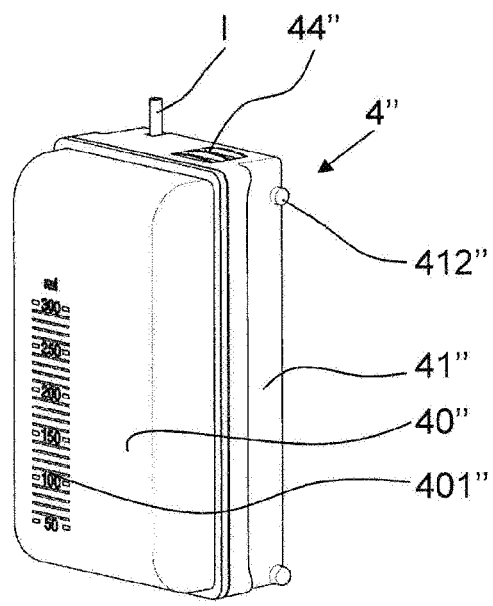
FIG. 22    FIG. 23

US 11,090,417 B2

SUCTIONING AND SUPPLY DEVICE WITH DRIVE UNIT AND CONNECTING PART

CROSS-REFERENCE TO RELATED APPLICATION

The present application is the US national phase of International Application No. PCT/EP2017/073464, filed Sep. 18, 2017, which claims priority to European Application No. 16189674.1, filed Sep. 20, 2016. The priority application, EP 16189674.7, is hereby incorporated by reference in its entirety.

TECHNICAL FIELD

The present invention relates to a device for suctioning bodily fluids and for supplying a substance to a human or animal body and also relates to a connecting part and to a drive unit of such a device. These types of devices are used, in particular, in the medical field, for example in negative pressure wound therapy combined with instillation or irrigation, in ophthalmic surgery or in liposuction.

PRIOR ART

In the medical field, there are diverse applications where, on the one hand, bodily fluids or secretions are suctioned from body cavities or wounds by means of a pump and, on the other hand, a substance is supplied to the body. Possible areas of application relate, in particular, to negative pressure wound therapy combined with instillation, ophthalmic surgery and liposuction (fat removal). Depending on the application, the suctioning and the supplying are effected in this case simultaneously, one after another and/or intermittently in an alternating manner.

The substance to be supplied can be, for example, a physiological or non-physiological saline solution, a drug or a mixture thereof. The substance can serve, for example, for promoting tissue repair, for preventing infection or for local anaesthesia. The supplying of the substance can consequently serve for rinsing or for therapeutic, diagnostic and/or preventive purposes.

Frequently for supplying the substance, in a similar manner as for conventional infusion, a liquid pouch or a bottle filled with the substance to be supplied is arranged elevated above the part of the body to be treated such that the substance is supplied through a supply line to the point to be treated on account of hydrostatic pressure. Separately to this, the bodily fluids are suctioned by a vacuum pump via a corresponding line.

In order to enable better adjustment and control when supplying the substance, and/or in order to be independent of the arrangement and in particular of the elevation of the liquid container filled with the substance, systems are also sufficiently well-known where the supplying of the substance to the body is effected by means of a pump, in particular a so-called peristaltic or hose pump.

For example, US 2016/0015873 discloses a therapy system with an instillation cartridge which comprises a pump for supplying instillation liquid to the body.

WO 2016/065335 discloses a device with a pneumatically driven instillation controller.

WO 2015/091070 discloses, just as US 2008/0154184, US 2008/0154182, U.S. Pat. No. 8,591,453 and US 2008/0154185, a device with two pumps arranged in a common housing, one of which serves for suctioning bodily fluids and the other for supplying a substance.

US 2014/0163487 discloses a device with two pumps, in this case the pump head of a peristaltic pump, which serves for supplying a substance to the body, being arranged on the outside surface of the pump unit housing. A liquid container which serves for receiving an instillation liquid is connectable to the pump unit housing. A tube guide is realized on the liquid container, on account of which tube guide the pump head, when the container is connected to the pump unit housing, exerts a corresponding pumping action on the instillation tube running out of the container interior in order to pump the instillation liquid toward the body in this manner.

Said devices, which serve, on the one hand, for suctioning bodily fluids and, on the other hand, for supplying a substance, are restricted to certain applications and in addition are in the majority of cases expensive and correspondingly cost-intensive to produce.

EP 0 293 081 discloses a device with a drive device which comprises a pump head arranged on the outside. A cassette with a tube guide is connectable in such a manner to the drive device that the pump head, in combination with a secretion line which runs in the tube guide, forms a peristaltic pump. By means of the peristaltic pump, secretions are able to be suctioned from the wound area through the secretion line. An infusion line for a conventional infusion is run through the cassette.

Documents FR 2 624 378, FR2624376 and FR2624377 disclose instillation containers for supplying an instillation liquid. A flexibly realized pouch, in which instillation liquid is received, is arranged in each case in the interior of the rigidly constructed containers. The instillation liquid is able to be conveyed out of the pouch by generating pressure in the container interior.

Further generic devices are disclosed, for example, in WO 2011/018132 and US 2016/0095964.

SUMMARY OF THE INVENTION

It is consequently an object of the invention to create a versatile device for suctioning bodily fluids and for supplying a substance to a human or animal body, which device is additionally cheap to produce. The device should additionally be simple to handle for the user.

In order to achieve this object, the present invention provides a device for suctioning bodily fluids and for supplying a substance to a human or animal body, said device comprising
a drive unit having a drive,
a pump head which is drivable by the drive and
a connecting part which is releasably, i.e. preferably without the help of a tool, connectable to the drive unit and has a tube guide which is realized in such a manner for receiving a tube that the tube, when the connecting part is connected as intended to the drive unit, in combination with the pump head, forms a peristaltic pump by way of which the fluid substance is conveyable through the tube to the human or animal body.

The pump head is incorporated in the connecting part and the drive unit comprises a coupling element which is connected to the drive and couples the pump head to the drive when the connecting part is connected as intended to the drive unit.

By incorporating the pump head in the connecting part, the device is considerably more versatile. Thus, for example, various connecting parts with different pump heads can be connected to the same drive unit. The pump head can be adapted specifically to the respective connecting part as regards its dimensioning and development. The connecting parts, for example, can include different substances and/or serve for different applications. By designing the pump head in a corresponding manner, different requirements can be met easily and always by using the same drive unit.

In addition, the demands on the connecting part with respect to the service life thereof are often less stringent than the corresponding demands on the drive unit. As a result of incorporating the pump head in the connecting part, the less stringent demands with respect to service life also apply to the pump head, which is consequently considerably cheaper to produce than in the case of a device with a pump head that is incorporated in the drive unit.

The device according to the invention is used for medical purposes, in particular for the negative pressure treatment of wounds combined with instillation or irrigation on the human or animal body. However, other areas of application are possible, for example for combined fat removal and flushing in the case of liposuction or for the flushing of catheters to avoid blockages or for combined suctioning and flushing in ophthalmic surgery.

The device is preferably configured for both suctioning bodily fluids and supplying a substance at the same time.

Peristaltic pumps are also known under the name of hose pumps and are also suited particularly well for conveying small fluid volumes of a substance, in particular of a fluid substance such as a liquid, in a controlled manner to the body. In addition, contamination of the fluid substance and of the device can also be ruled out in the case of peristaltic pumps. A peristaltic pump usually comprises at least one rotatably mounted pump head and a tube mounted in a tube bed. Usually, the tube guide forms the tube bed of the peristaltic pump. Usually mounted on the pump head are pressing rollers or sliding shoes which mechanically deform the tube that is mounted in the tube bed when the pump head rotates and, as a result, convey a substance through the tube.

For example, an installation line can be inserted in such a manner into the tube guide that is realized on the connecting part that it is guided around the pump head at least in part such that said pump head is able to deform the tube of the installation line mechanically and convey a substance contained therein. The substance can be stored, for example, in a liquid pouch that is arranged above the peristaltic pump or in a correspondingly arranged bottle and supplied therefrom.

The drive, usually, is a motor, in particular an electric motor. In a particularly preferred embodiment it is a brushless DC motor, as such a motor can usually be operated at low speeds of less than 100 rpm. A brushless DC motor additionally permits pressure control at relatively small amplitude, as a result of which it is possible to control the pressure (negative pressure or overpressure) in a very precise manner.

In a particularly preferred embodiment, the connecting part is a fluid-collecting container for collecting the suctioned bodily fluids or part of such a fluid-collecting container for collecting the suctioned bodily fluids or an intermediate part which is connectable to such a fluid-collecting container for collecting the suctioned bodily fluids in order to produce a connection between the drive unit and the fluid-collecting container. In the case of an intermediate part, said part therefore serves in particular for the purpose of connecting the fluid-collecting container operatively to the drive unit. As the fluid-collecting container is usually disposed of or replaced after a certain period of use, often even after a single use, where the connecting part is realized as a fluid-collecting container or as part thereof, it can be ensured that the pump head is replaced then too. The requirements for producing the pump head are considerably reduced as a result such that the device is overall cheaper to produce.

The connecting part can be realized as a fluid-collecting container, as part of a fluid-collecting container or as an intermediate part irrespective of whether the pump head is incorporated in the connecting part or not, and of whether or not the drive unit comprises a coupling element which is connected to the drive for coupling the pump head to the drive. The mentioned advantages are also achieved when the connecting part is realized, as specified, as a fluid-collecting container, as part of a fluid-collecting container or as an intermediate part and the pump head is not arranged on the connecting part, but on the drive unit. When the connecting part is connected to the drive unit, the pump head then rests in such a manner in the region of the tube guide that, in combination with a tube inserted into the tube guide, it forms a peristaltic pump. The realization of the connecting part as a fluid-collecting container, as part of a fluid-collecting container or as an intermediate part consequently provides a further independent invention.

The connecting part can also be an installation container which serves for providing the fluid substance. An installation line, which opens out into the interior of the installation container and consequently leads out of said container, is usually inserted into the tube guide that is provided on the connecting part such that by means of the peristaltic pump, the fluid substance can be conveyed through the installation line out of the installation container.

The connecting part can also be a container which serves both for collecting the suctioned bodily fluids and for providing the fluid substance. Such a container comprises in a preferred manner an interior which is divided into a first region for collecting the suctioned bodily fluids and into a second region for providing the fluid substance. The two regions can be separated from one another by means of a rigid partition wall. In a preferred manner, however, they are separated from one another by means of a flexibly realized partition wall. The container can be, in particular, a combined fluid-collecting and instillation container. The flexibly realized partition wall causes an enlargement of the first region to be directly produced by a reduction in the second region. The overall volume of the interior, which essentially corresponds advantageously to the sum of the volumes of the first and of the second regions, remains constant in this case. During operation of the device, the first region is usually filled gradually with the suctioned bodily fluids. Whilst the fluid substance is being supplied to the body, the second region is gradually emptied, as a result of which its volume is reduced. The flexible volumes of the first and of the second regions enable considerable space saving in comparison, for example, with a solution with a first rigid container for collecting the suctioned bodily fluids and a second rigid container for providing the fluid substance. In the ideal case, when the fluid substance is suctioned faster than or equally as fast as the bodily fluids from the container, this can even result in the volume being able to be halved.

The mentioned container with an interior which is divided by means of a flexible partition wall into a first region for collecting the suctioned bodily fluids and into a second region for providing the fluid substance, provides a further independent invention. Such a container can also be used in the case of conventional devices, in particular conventional instillation or irrigation devices where, on the one hand, bodily fluid is suctioned off and, on the other hand, a fluid substance is supplied to a human or animal body. The container does not necessarily have to have a pump head of a peristaltic pump for supplying the fluid substance or a tube guide which interacts with such a pump head. The container can be connected, for example, to a pump unit only via tube connections, and the fluid substance can also be supplied to the body without the aid of a pump, for example, by utilizing gravity by arranging the container above the body.

The flexible partition wall is formed in an advantageous manner by a pouch that is arranged in the interior. The pouch therefore then separates the first region from the second region. In a preferred manner, the pouch delimits the first or the second region, preferably however the second region, to a predominantly large extent. The pouch therefore preferably serves for providing the fluid substance.

The container which serves both for collecting the suctioned bodily fluids and for providing the fluid substance and has two regions that are separated by a flexible partition wall, comprises in an advantageous manner a vacuum connection for connection of a vacuum line in order to generate a vacuum in the first region of the interior. In addition, the container comprises in an advantageous manner a secretion line connection for connection of a secretion line which runs to the human or animal body in order to suction the bodily fluids through the secretion line into the first region by means of the vacuum generated in the first region of the interior. In addition, the container preferably comprises a connection for connection of a supply line in order to supply the fluid substance from the second region of the interior through the supply line to the human or animal body.

In particular, when the connecting part is an instillation container or a combined fluid-collecting and instillation container, but also in other cases, the connecting part can comprise an identification feature and the drive unit can comprise an identification unit in order to identify which type of connecting part is connected to the drive unit. The drive unit can then be realized, in particular, for the purpose of selecting or pre-selecting one of several possible operating modes for driving the peristaltic pump in dependence on the identified connecting part. In the event of the connecting part being an instillation container or a combined fluid-collecting and instillation container, the identification feature can serve, in particular, for identifying the type of substance contained in the container.

In a particularly preferred embodiment, the connecting part is a disposable part which is designed for one-off use and in an advantageous manner is produced substantially completely from injection moulded parts. In the case of a disposable part which is replaced and disposed of after a certain time, for example when the fluid-collecting container is full or the instillation container is empty, the demands in particular on a pump head that is possibly incorporated therein are relatively small. The production costs for the entire device can be reduced considerably as a result compared to a device where the pump head is arranged in or on the pump unit housing and as a result has to be designed for a much longer service life.

In order to adapt the rotational speed of the pump head in relation to that of the drive, a gearing unit, in particular a planetary gearing unit, can be provided, via which the pump head is coupled to the drive when the connecting part is connected as intended to the drive unit. The gearing unit can be incorporated, in particular, in the connecting part.

The drive unit can additionally comprise a vacuum pump, in particular a diaphragm pump, which serves for suctioning the bodily fluids. In an advantageous manner, the vacuum pump forms part of the drive unit. A diaphragm pump usually comprises at least one diaphragm as well as one pump chamber which is delimited by said diaphragm.

In a preferred manner, the drive unit comprises a housing in which both the drive and the vacuum pump are arranged. The coupling element is advantageously arranged on an outside surface of the housing.

In a preferred embodiment, the same drive which serves for driving the peristaltic pump also serves for driving the vacuum pump. By the same drive serving for driving both pumps, the device is able to be dimensioned in a smaller manner overall and additionally be lighter in weight. As a result, the device can be realized in such a manner, in particular, that it is portable, that is to say that it is able to be carried comfortably by a user on their own and without excessive effort being required. Advantageously, the device is additionally designed in an overall compact manner. On account of the only one drive, the susceptibility to errors is also reduced, and the device can also be produced overall in a more cost-efficient manner.

In a preferred manner, the pump head is coupled to the drive via at least one freewheel when the connecting part is connected as intended to the drive unit. Usually, the freewheel is accommodated in the pump unit housing, but could also be incorporated, in principle, in the connecting part. If the same drive serves both for driving the peristaltic pump and for driving a vacuum pump, the freewheel can in particular, depending on the direction of rotation of the drive, cause either both pumps to be driven together, or only the peristaltic pump or only the vacuum pump to be driven. This can be desirable for certain applications.

A first freewheel, for example, can couple the peristaltic pump to the drive. In certain embodiments, there can also be a second freewheel, by means of which the vacuum pump is coupled to the drive. The second freewheel advantageously comprises a direction of freewheeling that is opposite to that of the first freewheel. As a result, it can be ensured, in particular, that either the first pump or the second pump is driven depending on the direction of rotation, but not the two together. This means that either a substance is supplied to the body or bodily fluids are suctioned off, but not the two at the same time.

The first and, if present, the second freewheel can be, for example, a clamping bodily freewheel, a wrap spring clutch (spring coil freewheel) or a self-synchronizing clutch coupling.

In particular, when the drive serves both for driving the peristaltic pump and for driving the vacuum pump, but also when the drive serves only for driving the peristaltic pump, the device can additionally comprise a valve, in particular, a pneumatic valve, by means of which the vacuum pump is connectable to the environment in order to suck in air from the surroundings at least in part or even completely instead of bodily fluids. This leads to a reduction in or even elimination of the suction effect of the vacuum pump in the system. The valve can be connected, in particular, to a vacuum connection of the vacuum pump, to which a suction line is connectable. The vacuum connection can be connected to the environment instead of to the suction line, where required, at least in part or even completely by means of changing over the valve. The valve makes it possible to vary the suction performance for suctioning off bodily fluids whilst keeping the motor power constant.

BRIEF DESCRIPTION OF THE DRAWINGS

Preferred embodiments of the invention are described below by way of the drawings which simply serve for explanation and are not to be seen as restricting, and in which:

FIG. 20 shows a first perspective view of the instillation container of the device of FIG. 19;

FIG. 21 shows a perspective view of the instillation container of the device of FIG. 19, the cover of the pump head having been omitted;

FIG. 22 shows a perspective view of the base part of the instillation container of the device of FIG. 19;

FIG. 23 shows a second perspective view of the instillation container of the device of FIG. 19;

DESCRIPTION OF PREFERRED EMBODIMENTS

FIGS. 1 to 33 show different embodiments of devices according to the invention. The devices shown in FIGS. 1 to 33 are suitable, in particular, for the combined negative pressure and instillation/irrigation treatment of wounds on the human or animal body. Accordingly, the following explanations refer in each case to the use of the devices in combined negative pressure and instillation/irrigation treatment. It would also be possible, in principle, however, to use said devices, with the correspondingly adapted design, for catheter flushing, ophthalmic surgery, liposuction or another medical application.

Elements with an identical or similar technical function and action are provided in each case in the different embodiments in FIGS. 1 to 33 with the same references or they comprise the same reference but provided with an apostrophe (').

The device of the first embodiment according to the invention, which is shown in FIGS. 1 to 7, comprises a pump unit housing 1 (FIG. 1) with a connecting part in the form of a fluid-collecting container 5 (FIGS. 2 and 6) that is connectable thereto.

Figure 1:
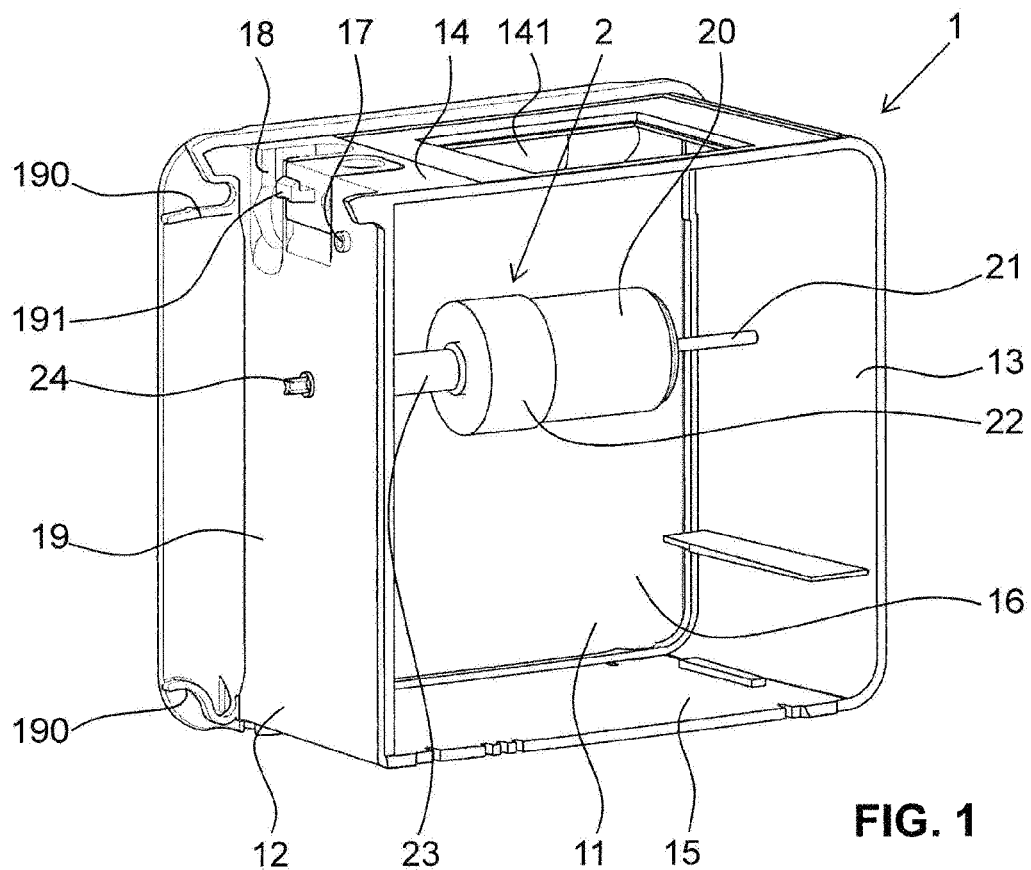
FIG. 1 shows a perspective view of a schematically shown pump unit housing of a device according to an embodiment according to the invention, the front wall having been omitted.

The pump unit housing 1 has an overall substantially cuboid shape with a front wall that is not shown in FIG. 1, a rear wall 11, a first side wall 12 and a second side wall 13 as well as a top wall 14 and a bottom wall 15. The front wall and the rear wall 11 comprise one wall edge each, which wall edges protrude from the first side wall 12 that is arranged in between them. The fluid-collecting container 5 is held between said wall edges and as a result can be fastened easily, nevertheless securely and in a protected manner, to the pump unit housing 1.

For suspending and holding the fluid-collecting container 5 on the pump unit housing 1, receiving hooks 190, in which correspondingly realized and arranged pins 554 of the fluid-collecting container 5 are able to engage, are provided on the pump unit housing 1. The fluid-collecting container 5 is secured on the pump unit housing 1 by means of a retaining lug 191 which is mounted on a spring-loaded element and is realized for snapping-into a latching notch 553 that is realized on the fluid-collecting container 5. In order to release the latching connection between the retaining lug 191 and the latching notch 553, the spring-loaded element, on which the retaining lug 191 is mounted, can be pressed downward against the spring force.

The protruding wall edges of the front wall and of the rear wall 11 as well as the receiving hooks 190 and the retaining lug 191 together form a container receiving means 19 of the fluid-collecting container 5.

The pump unit housing 1 comprises a housing-side vacuum connection 17 which, when the fluid-collecting container 5 is mounted on the pump unit housing 1, is coupled to a container-side vacuum connection 551 which is correspondingly provided on the fluid-collecting container 5 so that via the connections 17 and 551 a vacuum can be generated in the interior of the fluid-collecting container 5 in order to suck bodily fluids in via a secretion line (not shown in the Figures) and to collect them in the fluid-collecting container 5. The secretion line connects the fluid-collecting container 5 to a cavity or wound of a patient, from which bodily fluids are to be suctioned.

In addition, an adapter receiving means 18, which serves for receiving a tube adapter which is not shown in the Figures, is provided inside the first side wall 12. The tube adapter connects the secretion line to the interior of the fluid-collecting container 5 via a container-side secretion connection 552 which is provided on the fluid-collecting container 5.

A drive train 2 with a motor 20 and a motor shaft 21 which is connected to the motor 20 is accommodated in an interior 16 of the pump unit housing 1. The pump unit housing 1 forms a drive unit together with the drive train 2 and with further elements arranged, if needs be, in the interior 16.

By way of a first end region, the motor shaft 21 directly drives a diaphragm pump which is not shown in FIG. 1 for reasons of representation. The diaphragm pump is arranged in the interior 16 of the pump unit housing 1. By way of a second end region which cannot be seen in FIG. 1, the motor shaft 21 is connected to a freewheel and/or a gearing unit 22 which connects the motor shaft 21 to a drive shaft 23. The drive shaft 23, which extends along the rotational axis of the motor shaft 21, projects through the first side wall 12.

On the outside surface of the pump unit housing 1, a coupling element 24 is mounted so as to be non-rotatable on the end of the drive shaft 23. The coupling element 24 is in the form of a toothed wheel. In the present case, it is a toothed wheel with four teeth. A pump head 30, incorporated in the fluid-collecting container 5, of a peristaltic pump 3 can be driven via the coupling element 24 when the fluid-collecting container 5 is mounted as intended on the pump unit housing 1.

The motor 20 consequently serves both for driving the diaphragm pump and for driving the peristaltic pump 3. In an alternative embodiment, two separate motors can obviously also be provided in the interior 16 of the pump unit housing, one serving for the drive of the diaphragm pump and the other for the drive of the peristaltic pump 3.

Figure 2:
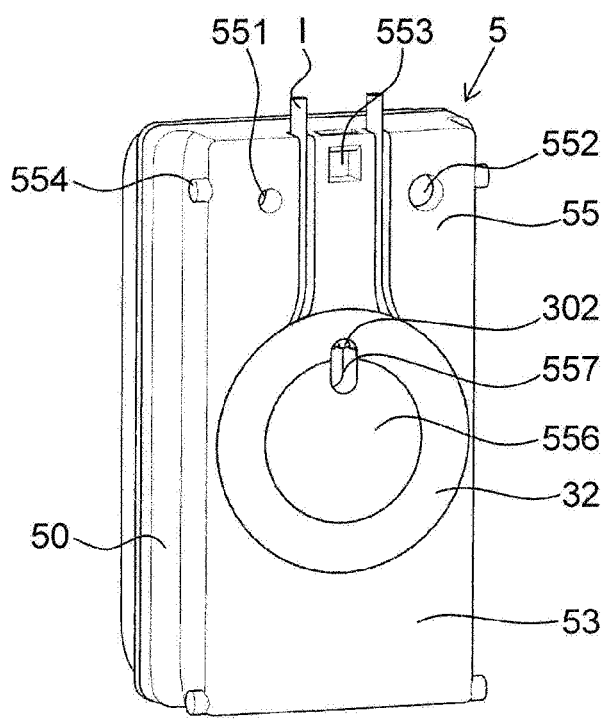
FIG. 2 shows a first perspective view of a fluid-collecting container which is suitable for connection to the pump unit housing of FIG. 1.
Figure 3:
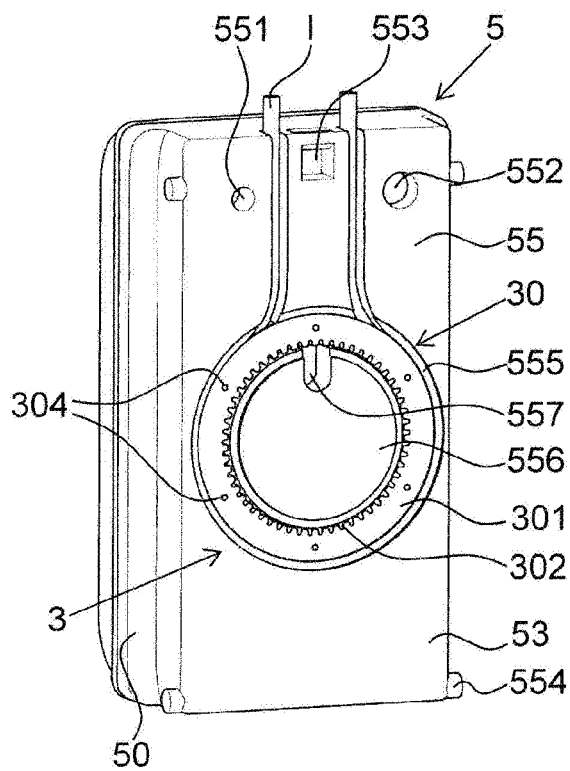
FIG. 3 shows a perspective view of the fluid-collecting container of FIG. 2, the cover of the pump head having been omitted.
Figure 4:
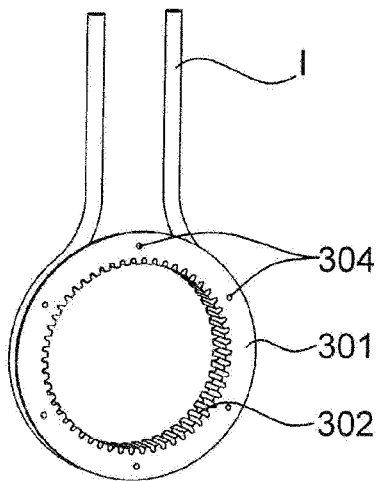
FIG. 4 shows a first perspective view of only the pump head as well as of the instillation line of the fluid-collecting container of FIG. 2.
Figure 5:
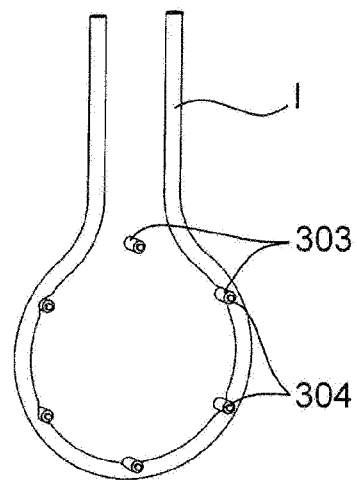
FIG. 5 shows a perspective view of parts of the pump head as well as of the instillation line of the fluid-collecting container of FIG. 2.
Figure 6:
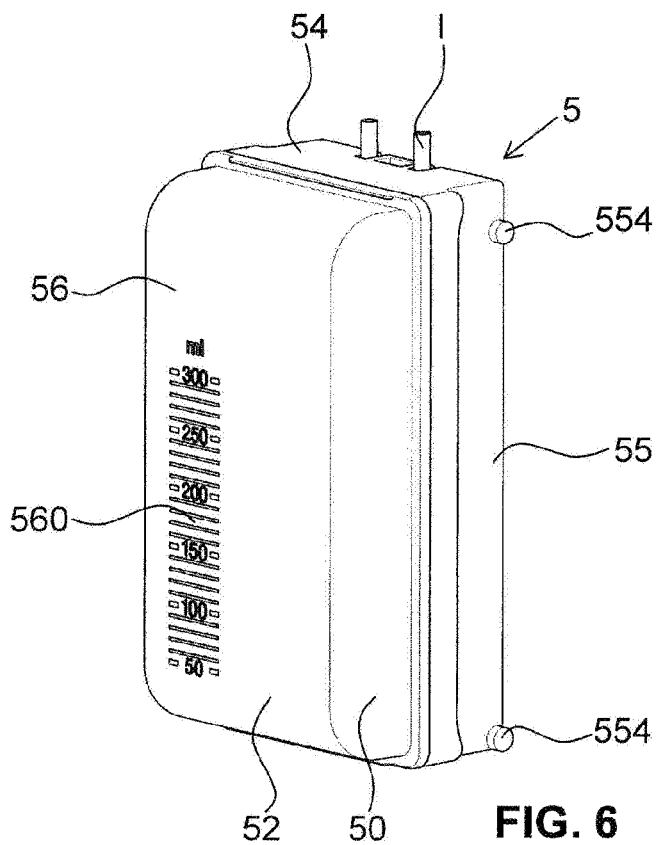
FIG. 6 shows a second perspective view of the fluid-collecting container of FIG. 2.
Figure 7:
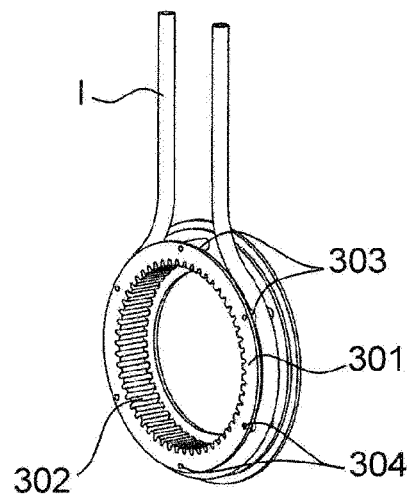
FIG. 7 shows a second perspective view of only the pump head as well as of the instillation line of the fluid-collecting container of FIG. 2.
Figure 8:
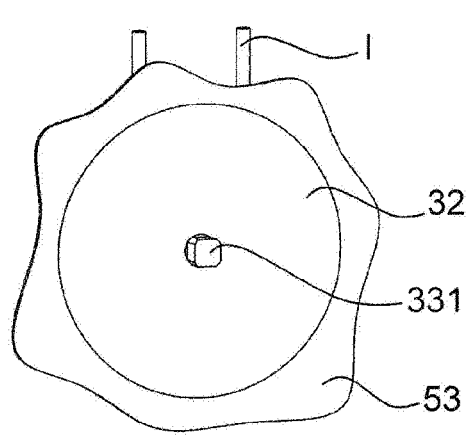
FIG. 8 shows a first perspective part view of the region of the pump head, covered with a cover, of a fluid-collecting container according to a variant.
Figure 9:
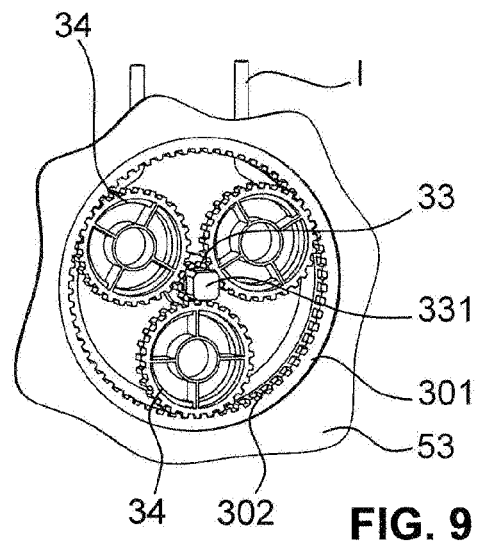
FIG. 9 shows a perspective part view of the region of the pump head, realized at least in part as a planetary gearing unit, of the fluid-collecting container of FIG. 8, without a cover.
Figure 10:
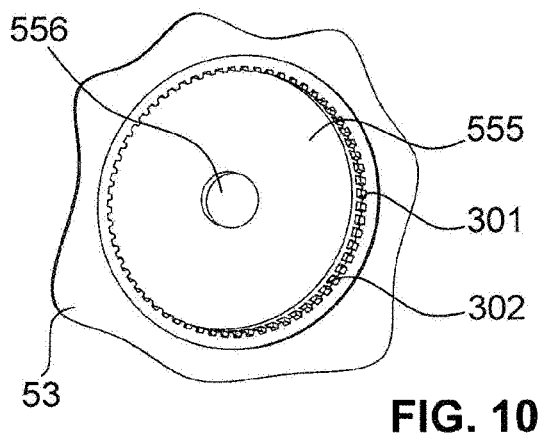
FIG. 10 shows a perspective part view of the region of the pump head of the fluid-collecting container of FIG. 8, without a planetary gearing unit and without a cover.
Figure 11:
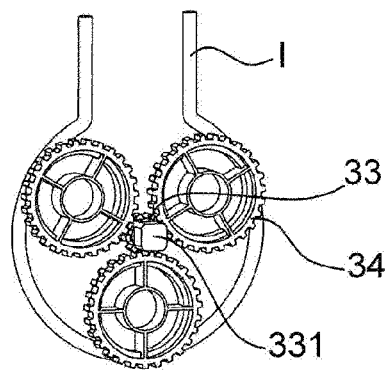
FIG. 11 shows a first perspective view of the planetary gearing unit, forming at least in part the pump head, of the fluid-collecting container of FIG. 8, with an instillation line.
Figure 12:
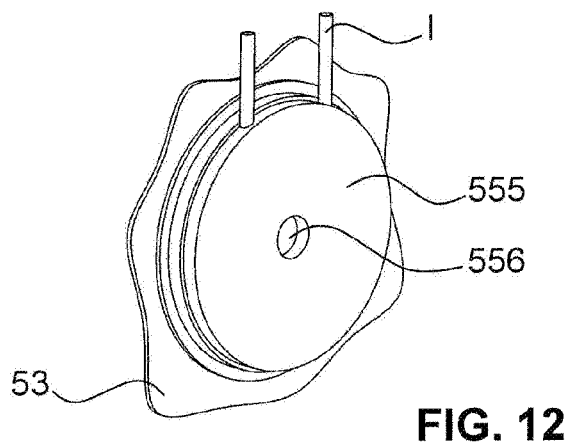
FIG. 12 shows a second perspective view of the region of the pump head of the fluid-collecting container of FIG. 8.
Figure 13:
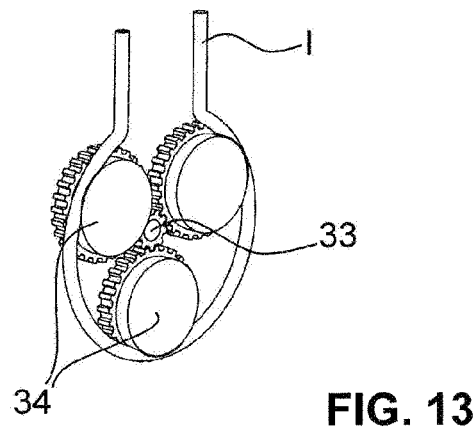
FIG. 13 shows a second perspective view of the planetary gearing unit, forming at least in part the pump head, of the fluid-collecting container of FIG. 8, with an instillation line.

The fluid-collecting container 5 comprises, as can be seen particularly well in FIGS. 2 and 6, a front wall 50, a rear wall that cannot be seen in the Figures, two side walls 52 and 53 as well as a top wall 54 and a bottom wall which cannot be seen either. Said walls are formed by a base part 55 that is produced from an opaque material and a transparent part 56.

A fill level graduation 560 is provided on the side wall 52 which is formed exclusively by the transparent part 56.

The side wall 53, which is formed exclusively by the base part 55, comprises a centrally arranged, ring-shaped indentation 555. Inside the ring-shaped indentation 555, the side wall 53 forms a concentrically arranged bearing pin 556 which comprises a top recess 557 which is upwardly open.

A hollow wheel 301, which is arranged so as to be freely rotatable about the bearing pin 556, is arranged in the ring-shaped indentation 555. Pressing rollers 303 are mounted on the hollow wheel 301 at regular intervals along the circumferential direction so as to be freely rotatable about in each case a roller axis 304 (see FIGS. 5 and 7). When the hollow wheel 301 is rotated, the pressing rollers 303 serve for rolling-off onto a tube that is inserted in the ring-shaped indentation 555 on the radial outside surface of the hollow wheel 301. The tube forms an instillation line I. By the pressing rollers 303 rolling-off along the tube, said tube is pressed against the radially inwardly turned inside wall of the ring-shaped indentation 555 such that, on account of the mechanical deformation of the tube, a fluid substance contained in the instillation line I is pressed through said tube and conveyed toward the wound area.

The substance to be conveyed through the instillation line I can be, for example, a physiological or non-physiological saline solution, a medicinal product or a mixture thereof. The instillation substance can serve for flushing a wound or a cavity. However, it can also serve for introducing a medical drug or for local anaesthesia of the wound area.

A circumferential toothing 302 is realized on the hollow wheel 301 on its radial inside surface. With the fluid-collecting container 5 mounted as intended on the pump unit housing 1, the toothing 302 moves into engagement with the coupling element 24 such that when the drive shaft 23 is rotated, the rotational movement is transmitted onto the hollow wheel via the coupling element 24.

The hollow wheel 301, which is usually covered by means of a ring-shaped cover 32, together with the pressing rollers 303 mounted thereon forms a pump head 30 of a peristaltic pump 3. In operation, the pump head 30 acts upon the tube inserted into the ring-shaped indentation in order to convey a fluid that is located therein. The ring-shaped indentation 555 consequently forms the tube bed of the peristaltic pump 3, into which the tube forming the instillation line I is inserted.

In order to guide the instillation line I toward the ring-shaped indentation 555 and away from it again, corresponding guide ducts, which extend in a linear manner and parallel to one another from the ring-shaped indentation 555 up to the top wall 54, are realized inside the first side wall 12 for receiving the instillation line I. Together with the guide ducts, the ring-shaped indentation forms a tube guide for the instillation line I.

In an advantageous manner, essentially all the parts of the fluid-collecting container 5, including the hollow wheel 301 and the pressing rollers 303 mounted thereon, are produced using the injection moulding method. As the fluid-collecting container 5 is usually a disposable part which is replaced and disposed of for reasons of hygiene as soon as the container is full, the demands on the pump head 30 incorporated therein are relatively small. The production costs for the entire device can be considerably reduced as a result compared to a device where the pump head is arranged in or on the pump unit housing and as a result has to be designed for a much longer service life.

Figure 14:
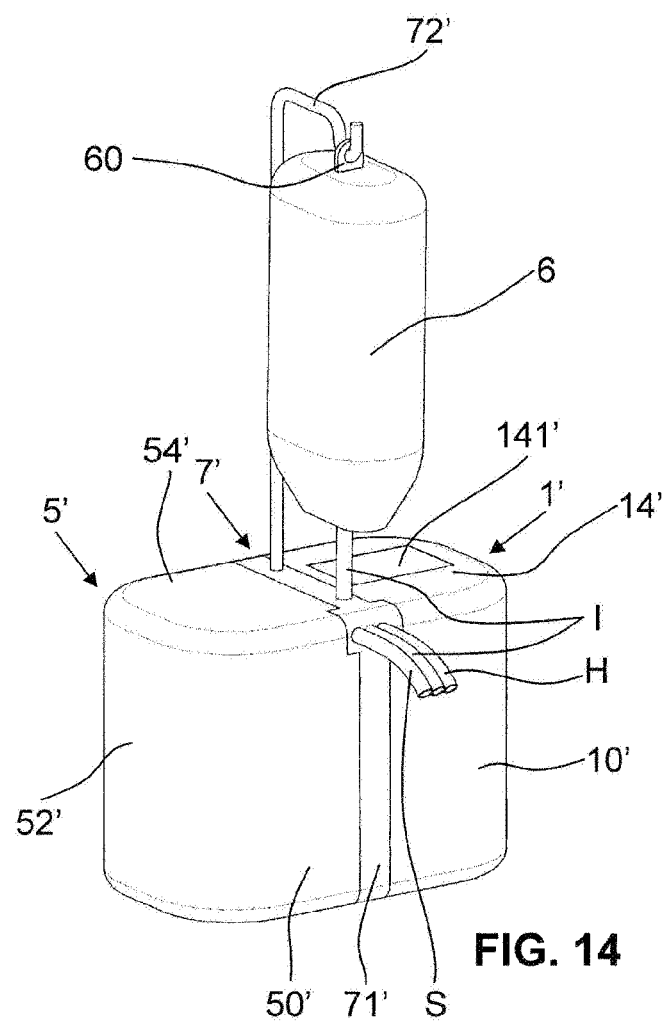
FIG. 14 shows a perspective view of a schematically shown device according to a further embodiment according to the invention.
Figure 15:
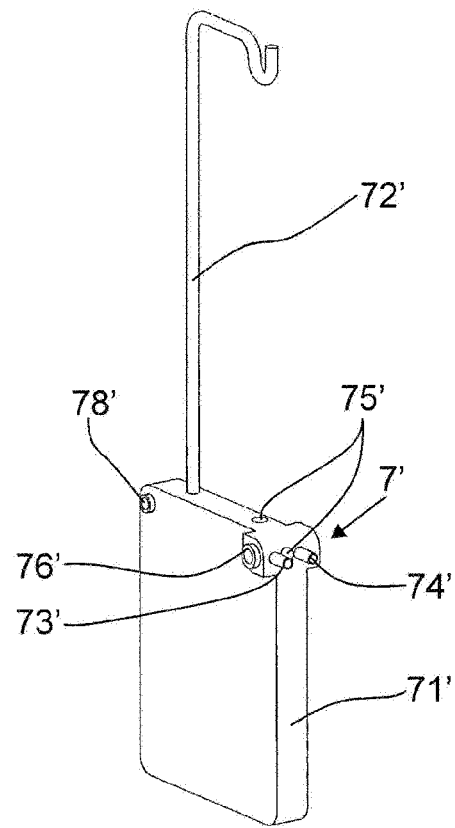
FIG. 15 shows a first perspective view of the peristaltic cassette of the device of FIG. 14, with a hanging bracket mounted thereon.
Figure 16:
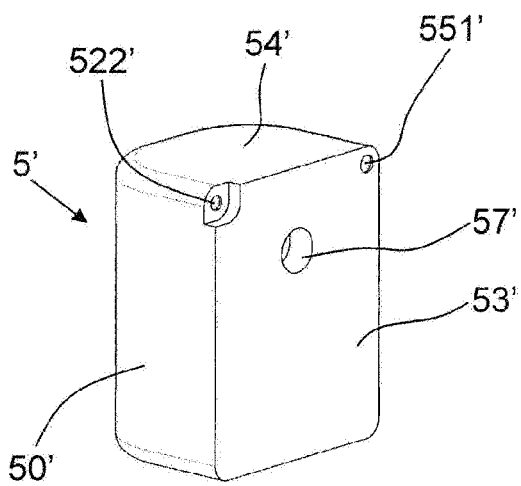
FIG. 16 shows a perspective view of the fluid-collecting container of the device of FIG. 14.
Figure 17:
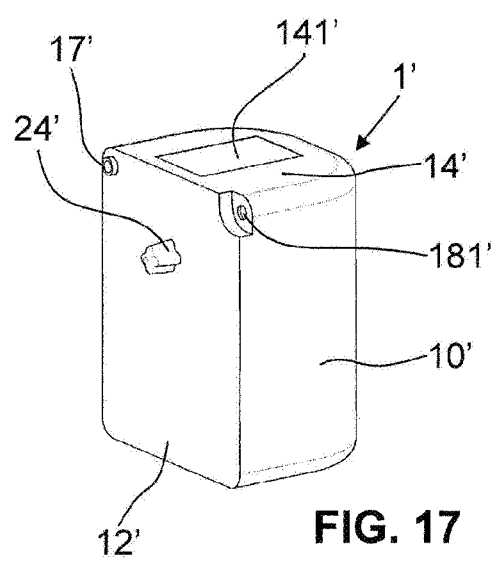
FIG. 17 shows a perspective view of the pump unit housing of the device of FIG. 14.

The instillation line I can be connected to a liquid container 6, such as the one shown in FIG. 14, in which an instillation liquid is stored. The liquid container 6, which can be realized in particular as a pouch, can comprise a hanger 60 in order to suspend it, for example, on an infusion stand above or close to the peristaltic pump 3 with reference to the direction of gravity.

A window 141 for a display and control panel is arranged in the region of the top wall 14 of the pump unit housing 1. The device can be operated by means of the display and control panel, and in particular the function of the motor 20 can be adjusted. In addition, the display and control panel can serve for displaying data on the status of the device, such as, in particular, the current pump output and cycles etc. The display and control panel can be realized, for example, as a touch screen.

FIGS. 8 to 13 show an embodiment which differs from the embodiment of FIGS. 1 to 7 only in the region of the peristaltic pump 3:

The coupling between the coupling element 24 and the pump head 30 is not effected here in an eccentric manner with respect to the pump head 30 as in the case of the embodiment in FIGS. 1 to 7, but is effected centrally. The coupling is effected via a coupling element 331, which is mounted centrally so as to be freely rotatable in a ring-shaped indentation 555 on the fluid-collecting container 5. The coupling element 331 is realized as an external square with a substantially quadratic cross section. The coupling element 24 which is provided on the side of the pump unit housing 24 is realized as an internal square in a correspondingly complementary manner thereto such that a rotational movement can be transmitted from the coupling element 24 to the coupling element 331.

The coupling element 331 is mounted non-rotatably and centrally on an inside wheel 33. The inside wheel 33 forms a centrally arranged toothed wheel of a planetary gearing unit 33, 34 and is in meshing engagement with three decentrally arranged outside wheels 34 which are also part of the planetary gearing unit 33, 34. The outside wheels 34, in turn, are in meshing engagement with the toothing 302 of the hollow wheel 301.

The entire planetary gearing unit 33, 34 as well as the hollow wheel 301 is coverable outwardly by means of a cover 32. Just the coupling element 331 projects toward the outside through an opening that is arranged centrally in the cover 32.

In the case of said embodiment, the outside wheels 34 form the pressing rollers to act upon the instillation line I in order to convey a substance contained therein to the wound area or to a body cavity.

In the case of the embodiment of a device according to the invention shown in FIGS. 14 to 18, a peristaltic cassette 7' is arranged as an intermediate part between a fluid-collecting container 5' and a pump unit housing 1'. The peristaltic cassette 7', which consequently forms a connecting part, comprises a housing 71' with a tube guide for the instillation line I which is run through the housing 71'. In addition, the peristaltic cassette 7' serves for connecting a secretion line S and an auxiliary line H to the device. Substantially all the parts of the peristaltic cassette 7' are advantageously produced from a plastics material using an injection moulding method.

The peristaltic cassette 7' has an overall substantially cuboid, thin external form. When the peristaltic cassette 7' is connected as intended to the pump unit housing 1' and to the fluid-collecting container 5', as is shown in FIG. 14, the fluid-collecting container 5', the peristaltic cassette 7' and the pump unit housing 1' together form an overall substantially cuboid form with rounded outside edges and corners. The outside faces of the peristaltic cassette 7' are then in each case arranged in alignment with the correspondingly adjoining outside walls of the pump unit housing 1', that is to say with a front wall 10', a rear wall, a first side wall 12', a second side wall, a top wall 14' and a bottom wall. In addition, the outside faces of the peristaltic cassette 7' are in each case arranged in alignment with the correspondingly adjoining outside walls of the fluid-collecting container 5', that is to say with a front wall 50', a rear wall, a first side wall 52', a second side wall 53', a top wall 54' and a bottom wall. The rear wall, the second side wall and the bottom wall of the pump unit housing 1' as well as the rear wall and the bottom wall of the fluid-connecting container 5' are not to be seen in the Figures.

The peristaltic cassette 7' connects the pump unit housing 1' and the fluid-connecting container 5' operatively with one another by connecting a housing-side vacuum connection 17' of the pump unit housing 1' in an air-tight manner to a container-side vacuum connection 551' which is correspondingly provided on the fluid-collecting container 5'. For this purpose, the peristaltic cassette 7' comprises a vacuum connection 78' which faces the fluid-collecting container 5' and a vacuum connection 79' which faces the pump unit housing 1' (see FIG. 15 or 18). The vacuum connections 78' and 79' are connected together in a fluidically communicating manner inside the peristaltic cassette 7'.

The peristaltic cassette 7' additionally comprises an auxiliary connection 77' (FIG. 18), which, when the peristaltic cassette 7' is connected as intended to the pump unit housing 1', is fluidically connected to a housing-side auxiliary connection 181' that is provided on the pump unit housing 1'. The auxiliary connection 77' is connected inside the housing 71' in a fluidically communicating manner to an auxiliary connection 74' of the peristaltic cassette 7' (FIG. 15) which serves for connecting an auxiliary line H. By means of the auxiliary line H, it is possible, where required, to flush the secretion line S and/or to measure the pressure in the secretion line S. In a preferred manner, the auxiliary line H opens out into the secretion line S in the vicinity of the cavity or wound for this purpose.

On its side facing toward the fluid-collecting container 5', the peristaltic cassette 7' comprises a first secretion connection 76' which is realized for coupling to a container-side secretion connection 552' that is provided on the fluid-collecting container 5' and is connected in a fluidically communicating manner to a second secretion connection 73' inside the housing 71'. The second secretion connection 73' serves for connection to a secretion line S in order to suck bodily fluids into the fluid-collecting container 5' through said line via the first secretion connections 76' and the container-side secretion connection 552'. To this end, a vacuum is generated in the interior of the fluid-collecting container 5' via the vacuum connections 17', 79', 78' and 551' by means of a vacuum pump that is arranged in the pump unit housing 1'.

Figure 18:
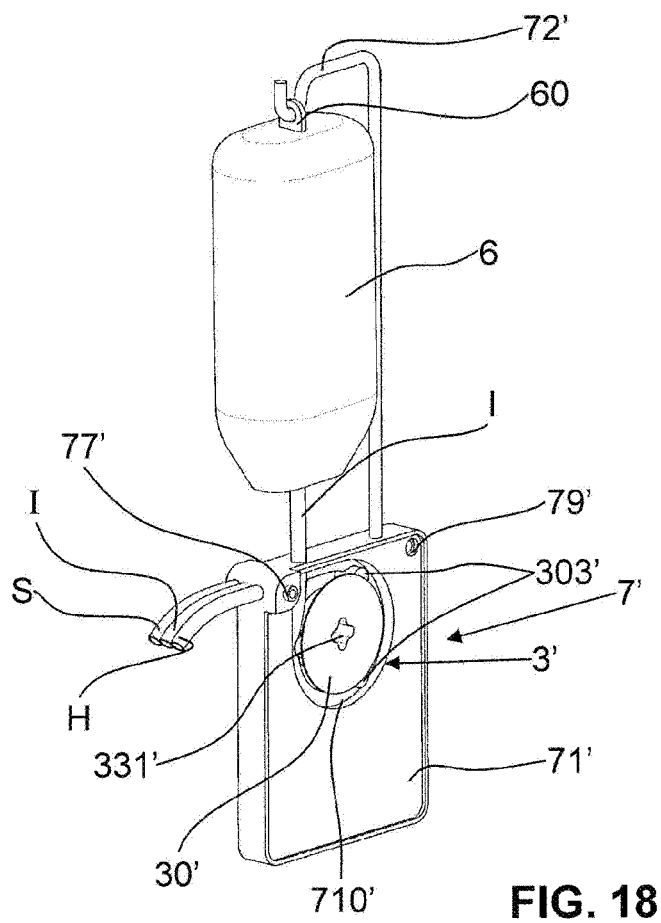
FIG. 18 shows a second perspective view of the peristaltic cassette of the device of FIG. 14, with a hanging bracket mounted thereon and a liquid container suspended on the hanging bracket.
Figure 19:
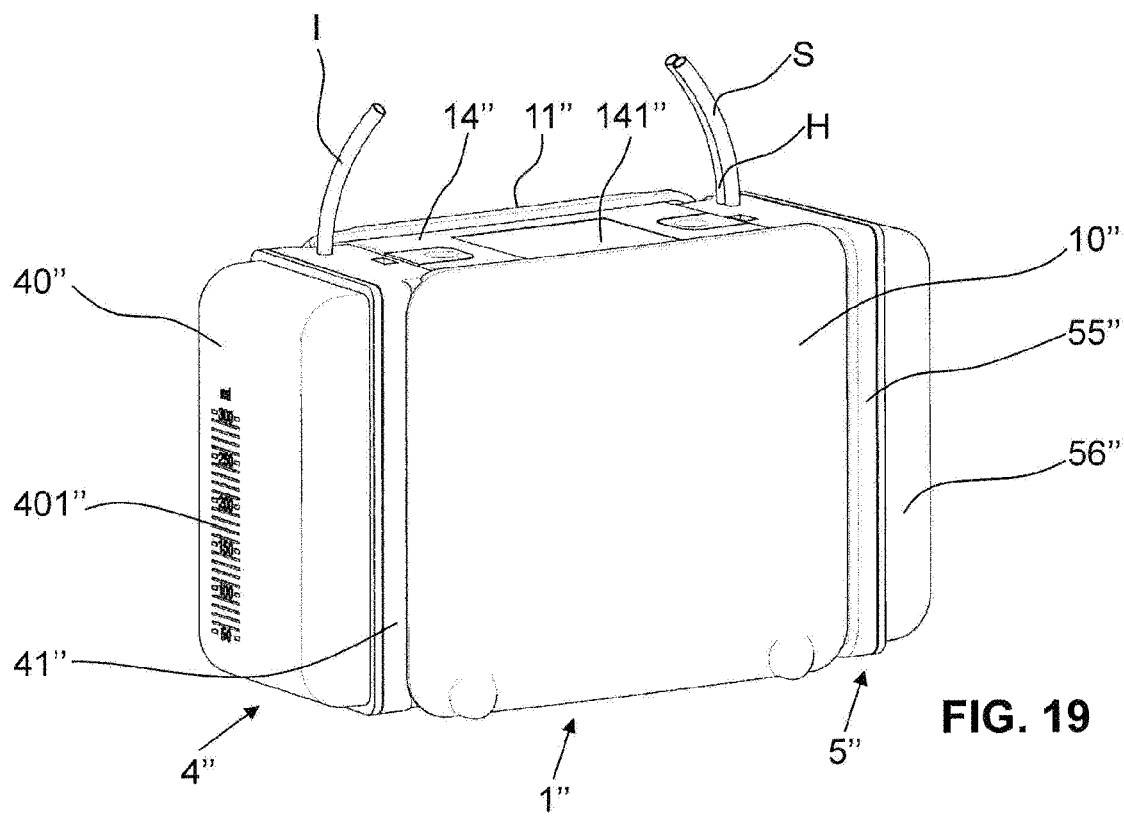
FIG. 19 shows a perspective view of a schematically shown device according to a further embodiment according to the invention.
Figure 24:
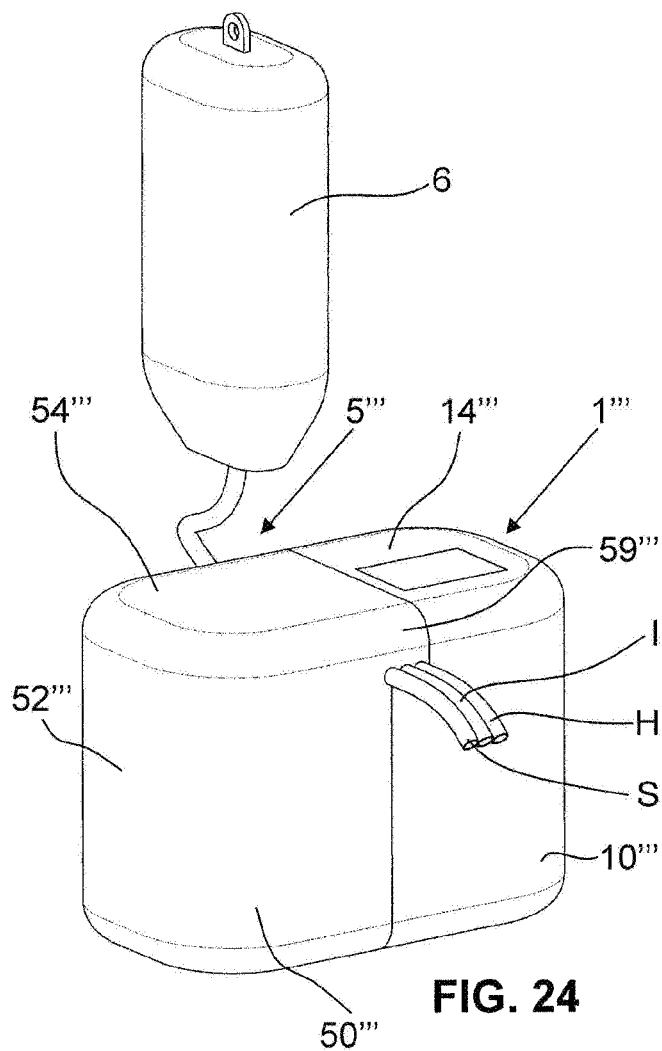
FIG. 24 shows a perspective view of a schematically shown device according to a further embodiment according to the invention.

On its side facing the pump unit housing 1', the housing 71' of the peristaltic cassette 7', as can be seen in FIG. 18, comprises a substantially circular indentation 710', inside which a pump head 30' of a peristaltic pump 3' is arranged so as to be freely rotatable. The pump head 30' comprises several pressing rollers 303' which serve for the purpose of rolling on the instillation line I that is placed around the pump head 30' in the indentation 710' and of supplying a substance through the instillation line I to the wound area by, at the same time, mechanically deforming the tube.

In order to transmit the rotational movement of a drive accommodated in the pump unit housing 1' to the pump head 30', the pump head 30' comprises a centrally arranged coupling element 331' in the form of an indentation. The indentation has a non-circular form which is realized in a complementary manner to a coupling element 24' that is arranged on the outside of the pump unit housing 1'. The coupling element 24' is non-rotatably mounted on a drive shaft which is realized for transmitting a rotational movement, which is brought about by the drive that is accommodated in the pump unit housing 1', onto the coupling element 24'.

A hanging bracket 72' is mounted on the peristaltic cassette 7' in order to suspend a liquid container 6 filled with instillation liquid by means of a hanger 60 above the peristaltic cassette 7' with reference to the direction of gravity. The instillation line I leading from the liquid container 6 is run from above through a first opening 75' into the peristaltic cassette 7', inside the indentation 710' around the pump head 30' and through a second opening 75' on the front side of the peristaltic cassette 7' back out of the same.

Operation of the device shown in FIGS. 14 to 18 is also possible without the peristaltic cassette 7', for example when it is only necessary to suction off bodily fluids, not however to supply a substance. The fluid-collecting container 5' is connected directly to the pump unit housing 1' for this purpose. The coupling element 24' is then arranged in an indentation 57' that is provided inside the side wall 53' of the fluid-collecting container 5' such that a possible rotational movement of the coupling element 24' remains ineffective. The housing-side vacuum connection 17' is coupled directly with the container-side vacuum connection 551'. An adapter, which is not shown in the Figures and comprises an auxiliary line connection that is connected to the auxiliary connection 181' as well as a secretion line connection which is connected to the secretion connection 551', is inserted between the housing-side auxiliary connection 181' and the container-side secretion connection 551'.

Operation of the device shown in FIGS. 14 to 18 is effected by means of a display and control panel that is arranged in a window 141' of the pump unit housing 1'.

A further embodiment according to the invention is shown in FIGS. 19 to 23 where not only a fluid-collecting container 5" can be fixed on a pump unit housing 1" and connected to the same, but also a further connecting part in the form of an instillation container 4".

The pump unit housing 1" is realized in a similar manner to that of FIG. 1 and differs from said pump unit housing in particular as a result of the front wall 10" and the rear wall 11" protruding with their vertical wall edges not only toward one side, but toward both sides, of the side wall that is arranged in each case in between. On one side of the pump unit housing 1" the fluid-collecting container 5" is held between the wall edges of the front wall 10" and of the rear wall 11" and on the other side, of the instillation container 4".

A top wall 14" of the pump unit housing 1" comprises a window 141" for a display and control panel for operating and displaying the operating status of the device.

The fluid-collecting container 5" comprises a largely identical development with a base part 55" and a transparent part 56" to that of the embodiment shown in FIGS. 1 to 7. The fluid-collecting container 5" is fastenable on the pump unit housing 1" by means of several pins 412". In contrast to the fluid-collecting container of FIGS. 1 to 7, however, there is no pump head incorporated in the fluid-collecting container 5" in the present case. In addition, the secretion line S and the auxiliary line H here are run outward through the fluid-collecting container 5"

The instillation container 4", which is advantageously produced largely completely from a plastics material using the injection moulding method and serves for providing an instillation liquid, is developed in a similar manner to the fluid-collecting container 5". It comprises a transparent part 40", which is provided with a fill level graduation 401", as well as a base part 41" which is produced from an opaque material.

A ring-shaped indentation 43", inside which a hollow wheel 301" is arranged (FIG. 21), is realized inside the side face of the instillation container 4" that faces the pump unit housing 1". The hollow wheel 301", on which are mounted pressing rollers which are rotatable about roller axes 304", forms a pump head 30" of a peristaltic pump 3".

The hollow wheel 301" is mounted so as to be freely rotatable on a bearing pin 410" which is provided concentrically inside the ring-shaped indentation 43". In order to enable a meshing engagement between a coupling element which cannot be seen in the Figures and a toothing 302" which is realized on the inside of the hollow wheel 301" in the radial direction, the bearing pin 410" comprises a recess 411" which is open in the radial direction toward the indentation 43". The indentation 43" and the hollow wheel 301" are covered toward the outside by means of a cover 32".

An instillation line I, which opens out via a mouth 42" into the interior of the instillation container 4", is inserted into a tube guide which is realized in a recessed manner in the base part 41". The tube guide is formed by a supply duct which extends from the mouth 42" to the ring-shaped indentation 43", the ring-shaped indentation 43" and a duct which runs upward away from the indentation 43". Inside the ring-shaped indentation 43" the instillation line I is placed in such a manner about the pump head 30" that when the pump head 30" is rotated, the instillation line I is mechanically deformed by means of the pressing rollers and, as a result, the instillation liquid is pumped out of the instillation container and to the wound area.

A ventilation opening 44" is additionally provided on the base part 41" in order to admit outside air into the instillation container 4" if the quantity of instillation liquid in the instillation container 4" becomes smaller when the device is operating.

FIGS. 24 to 27 show a further embodiment of a device according to the invention where, in contrast to the embodiments shown in FIGS. 1 to 23, the pump head 30''' of a peristaltic pump 3''' is not integrated in a connecting part, but in the pump unit housing 1'''. A fluid-collecting container 5''', which comprises a tube guide 559''' for guiding an instillation line I, is connectable to the pump unit housing 1''' such that the tube inserted into the tube guide forms a peristaltic pump 3''' in combination with the pump head 30'''.

Figure 25:
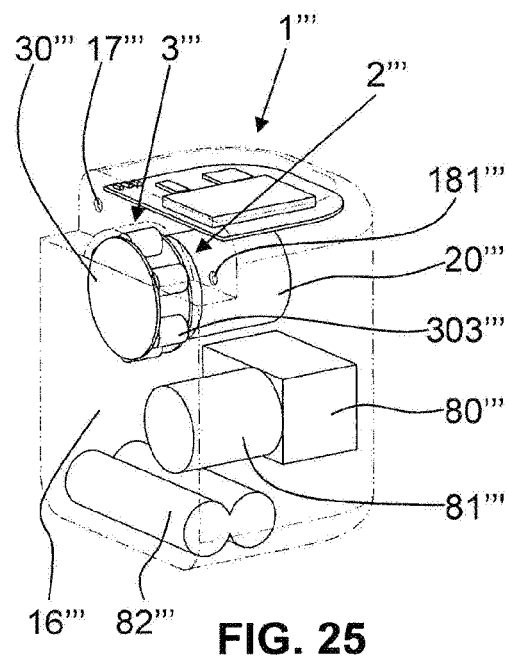
FIG. 25 shows a perspective view of the pump unit housing of the device of FIG. 24, the housing itself only being indicated by way of broken lines.
Figure 26:
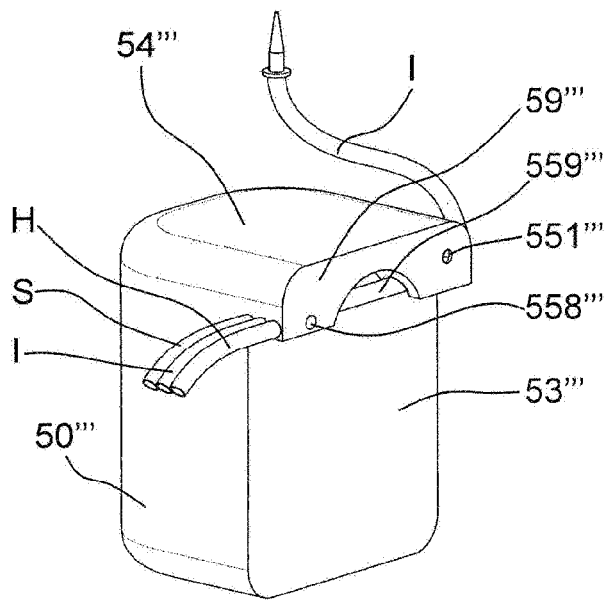
FIG. 26 shows a perspective view of the fluid-connecting container of the device of FIG. 24.
Figure 27:
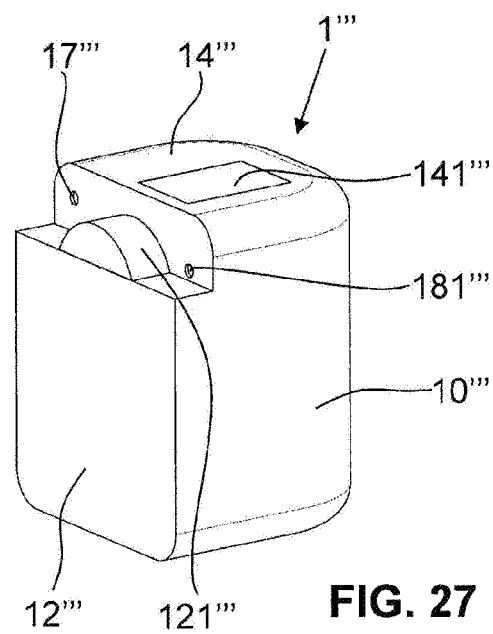
FIG. 27 shows a perspective view of the pump unit housing of the device of FIG. 24.
Figure 28:
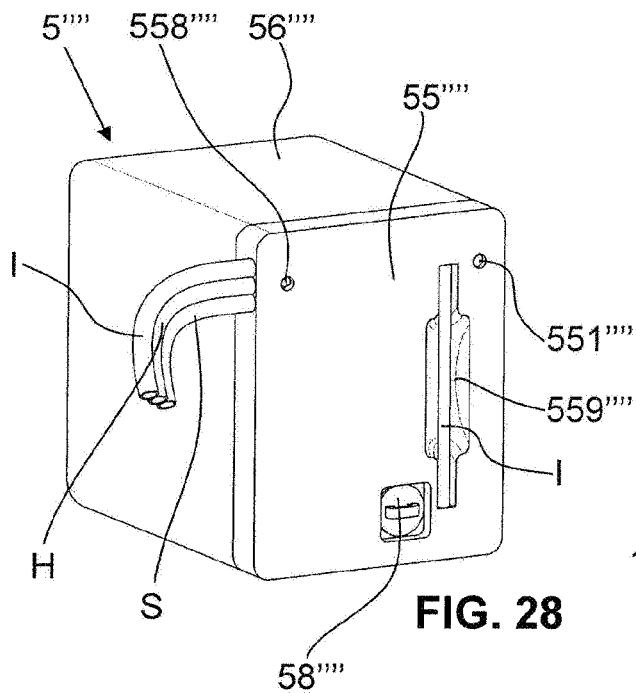
FIG. 28 shows a first perspective view of a fluid-collecting container of a device according to a further embodiment according to the invention.

As can be seen from FIG. 25, a motor 20''' of a drive train 2''', which serves for driving the pump head 30''' which is mounted fixedly on a motor shaft, is arranged in the interior 16''' of the pump unit housing 1'''. In addition, a diaphragm pump 80''' and a drive 81''' for driving said diaphragm pump 80''' are arranged in the interior 16'''. Supplying the drives 20''' and 81''' with electric energy is effected by means of an accumulator 82''' which is also arranged in the interior 16'''.

The diaphragm pump 80''' serves for suctioning off bodily fluids by a vacuum being generated in the fluid-collecting container 5''' via a vacuum connection 17''' which is provided on the pump unit housing 1''' and is connected to a vacuum connection 551''' of the fluid collecting container 5'''. As a result, the bodily fluids are sucked through a secretion line S into the interior of the fluid-collecting container 5''' and are collected in the same.

The pump unit housing 1''' comprises a top wall 14''' with a window 141''' for the arrangement of a display and control panel. A side wall 12''' lies flatly against the fluid-collecting container 5''', when the same is connected as intended to the pump unit housing 1'''.

The pump unit housing 1''' additionally comprises a housing-side auxiliary connection 181''' which, when the fluid-collecting container 5''' is mounted onto the pump unit housing 1''', is coupled with a container-side auxiliary connection 558''' provided on the fluid-collecting container 5''' in order to be connected in a fluidically communicating manner to an auxiliary line H. The auxiliary line H serves for flushing and/or measuring the pressure or the flow volume of the secretion line S.

The pump head 30''', on which several pressing rollers 303''' are mounted here too so as to be freely rotatable, is arranged in such a manner that at least one region of its circumferential face brings about a mechanical deformation of the instillation line I in operation when said instillation line is inserted into the tube guide 559''' of the fluid-collecting container 5''' and the fluid-collecting container 5''' has been connected as intended to the pump unit housing 1'''. The pump head 30''' can be exposed for this purpose with at least part of it circumferential face, or, as in the case of the present embodiment, can be covered there by a flexible covering membrane 121''' in order to prevent dirt particles ingressing into the pump head 30''' and into the interior 16'''.

In the region of the pump head 30''', the pump unit housing 1''' comprises a step, the upwardly turned face of which is projected through by the pump head 30'''. The step makes it possible for the pump head 30''' to act on the instillation line I inserted in the tube guide 559''' by way of a region of its circumferential face. Nevertheless, the pump unit housing 1''' and the fluid-collecting container 5''', which is connected as intended thereto, have together a substantially cuboid exterior shape. On account of the step, the front wall 10''' and the rear wall of the pump unit housing 1''', which is not visible in the Figures, are in each case realized in an L-shaped manner.

The fluid-collecting container 5''' comprises a first side wall 52''' as well as a second side wall 53''' which faces the pump unit housing 1''' and is projected over in the direction toward the pump unit housing 1''' by a top protruding region 59''', which also form a top wall 54''. As a result, the front wall 50''' and the rear wall that cannot be seen in the Figures are in each case in the form of an upside down L.

A circle-segment-like recess, which forms the tube bed of the instillation line I in the peristaltic pump 3''' and consequently the tube guide 559''', is provided on the side of the projecting region 59''' that faces downward, i.e. toward the pump head 30''. In operation, a substance is conveyable by means of the peristaltic pump 3''' through the instillation line I to the wound area or to a body cavity.

FIGS. 28 to 33 show a further embodiment of a device according to the invention having a pump unit housing 1'''' and a connecting part in the form of a fluid-collecting container 5'''' that can be connected thereto.

The fluid-collecting container 5'''' has a cuboid exterior form with a base part 55'''' and an advantageously transparent part 56''''. The base part 55'''' forms a cover which is removable from the transparent part 56'''' and forms the entire side face of the fluid-collecting container 5'''' that faces toward the pump unit housing 1''''. In an advantageous manner, the base part 55'''' is produced as one unit and substantially completely from a plastics material using an injection moulding method.

The vacuum line which runs from a vacuum pump that is accommodated in the pump unit housing 1'''' into the interior of the fluid-collecting container 5'''' extends via a housing-side vacuum connection 17'''' and a container-side vacuum connection 551'''' through the base part 55'''' when the fluid-collecting container 5'''' is connected as intended to the pump unit housing 1''''. In addition, a secretion line S opens out via the base part 55'''' into the interior of the fluid-collecting container 5''''. In addition, an auxiliary line H runs via a container-side auxiliary connection 558'''' that is realized on the base part 55'' and via a housing-side auxiliary connection 181'''' into the pump unit housing 1'''' when the fluid-collecting container 5'''' is connected to the pump unit housing 1''''. The auxiliary line H serves, where required, for flushing and/or measuring the pressure of the secretion line S.

The base part 55'''' comprises, on its side facing the pump unit housing 1'''', an indentation which is traversed by the tube of an instillation line I. The indentation forms the tube bed and consequently a tube guide 559'''' of a peristaltic pump 3'''' when the fluid-collecting container 5'''' is connected as intended to the pump unit housing 1''''.

Figure 29:
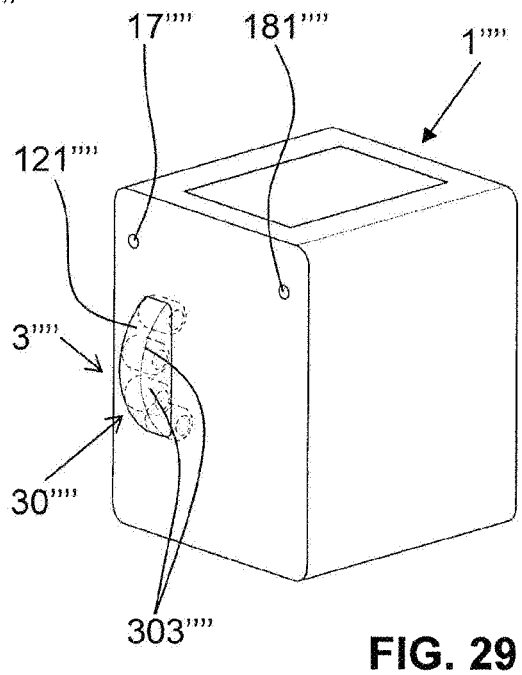
FIG. 29 shows a perspective view of a pump unit housing that is associated with the same device as the fluid-collecting container of FIG. 28.
Figure 30:
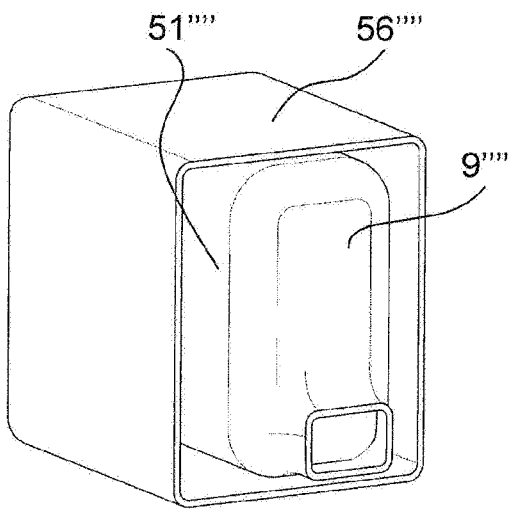
FIG. 30 shows a perspective view of the fluid-connecting container of FIG. 28, with the base part removed.
Figure 31:
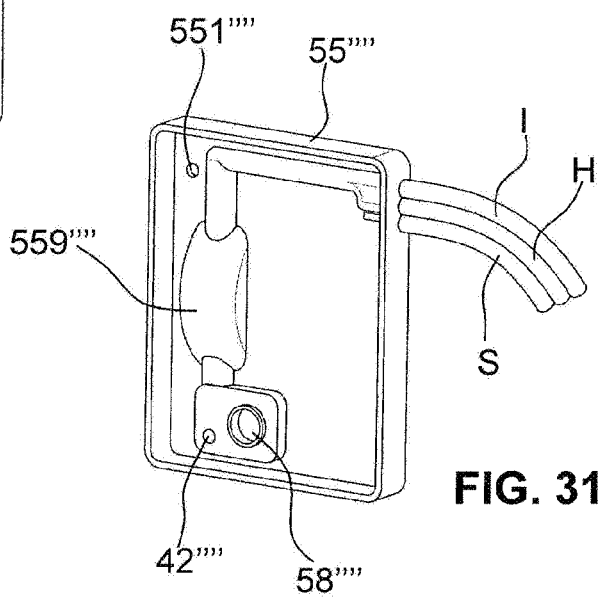
FIG. 31 shows a perspective view of the base part of the fluid-collecting container of FIG. 28.

The pump head 30'''' of the peristaltic pump 3'''' of said device is arranged in the pump unit housing 1'''' shown in FIG. 29, in which the pump head, at least with part of its circumferential face, projects outward toward the fluid-collecting container 5'''' through a corresponding side wall of the pump unit housing 1''''. Said projecting part of the pump head 30'''', from which only the pressing rollers 303'''' are shown in FIG. 29, can, as in the present case, be covered by a flexible covering membrane 121''''. When the fluid-collecting container 5'''' is connected to the pump unit housing 1'''', the pump head 30'''' projects into the indentation of the base part 55'''' forming the tube guide 559'''' and presses the instillation line I there against the base part 55''''.

The instillation line I that is run in the tube guide 559'''' opens out via a mouth 42'''' into a flexible liquid pouch 9'''' that is arranged in the interior 51'''' of the fluid-collecting container 5''''.

Figure 32:
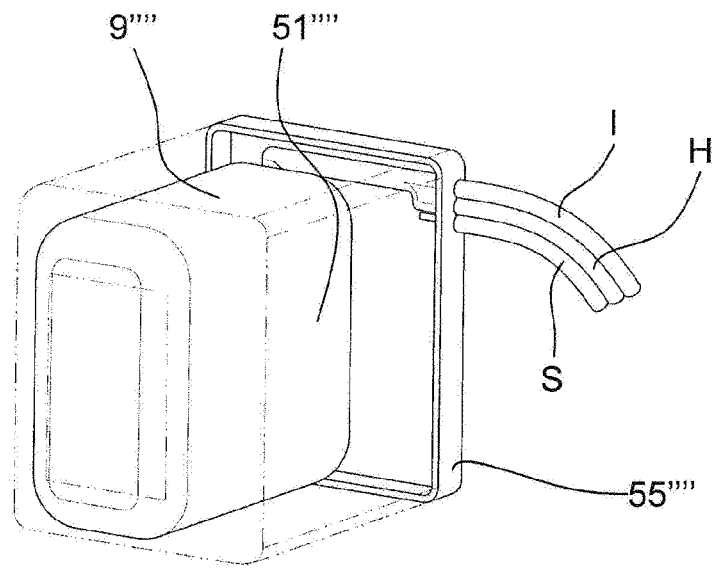
FIG. 32 shows a second perspective view of the fluid-collecting container of FIG. 28, the transparent part only being indicated by way of broken lines, in the state at the start of a treatment.
Figure 33:
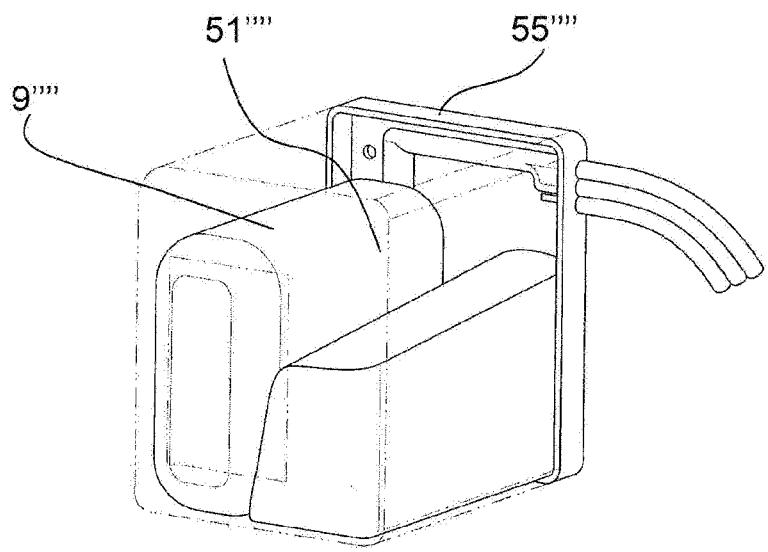
FIG. 33 shows a perspective view of the fluid-collecting container of FIG. 28, the transparent part only being indicated by way of broken lines, in the state after a certain length of time of treatment.

Instillation liquid, which is suppliable by means of the peristaltic pump 3'''' through the instillation line I to the body, is provided in the liquid pouch 9''''. FIG. 32 shows that at the start of a treatment, usually, only the liquid pouch 9'''' is filled. Over the duration of the treatment the liquid-collecting container 5'''' is filled increasingly with suctioned-off fluids, and the volume of the liquid pouch 9'''' is reduced by the fluids supplied to the body.

By means of a closure 58'''' that is arranged in the base part 55'''', the liquid pouch 9'''' can be emptied or filled without the base part 55'''' having to be removed from the transparent part 56''''.

The drives accommodated in the pump unit housings 1, 1', 1'', 1''' and 1'''' of FIGS. 1 to 33 can be, in particular, in each case a brushless DC motor. An accumulator can be provided in each case in the pump unit housing 1, 1', 1'', 1''' or 1'''' in order to supply the drive with electric power. In the case of all of the embodiments, the drive train between the drive and the pump head of the peristaltic pump can additionally comprise one or more gearing units in order to adapt the rotational speed of the pump head to that of the drive. The arrangement of a freewheel in the drive train is also possible in order to drive the pump head only when the drive comprises a certain rotational direction. By means of the at least one gearing unit and/or freewheel, the peristaltic pump and the vacuum pump, if both are drivable by one single common drive, can be operated arbitrarily at different or the same pump frequencies.

The invention claimed is:

1. A device for both suctioning bodily fluids and supplying a fluid substance to a human or animal body at the same time, said device comprising:
   a drive unit having a drive,
   a pump head which is drivable by the drive and
   a connecting part which is releasably connectable to the drive unit and has a tube guide which is realized in such a manner for receiving a tube that the tube, when the connecting part is connected as intended to the drive unit, forms, in combination with the pump head, a peristaltic pump by way of which the fluid substance is conveyable through the tube to the human or animal body,
   wherein the pump head is incorporated in the connecting part, and in that the drive unit comprises a coupling element which is connected to the drive and couples the pump head to the drive when the connecting part is connected as intended to the drive unit,
   and wherein the connecting part comprises a gearing unit via which the pump head is coupled to the drive when the connecting part is connected as intended to the drive unit.

2. The device according to claim 1, wherein the connecting part is a fluid-collecting container for collecting the suctioned bodily fluids or part of such a fluid-collecting container or an intermediate part which is connectable to such a fluid-collecting container in order to produce a connection between the drive unit and the fluid-collecting container.

3. The device according to claim 1, wherein the connecting part is an instillation container which serves for providing the fluid substance.

4. The device according to claim 1, wherein the connecting part comprises an identification feature and the drive unit comprises an identification unit in order to identify which type of connecting part is connected to the drive unit, and wherein the drive unit is realized for the purpose of selecting one of several possible operating modes for driving the peristaltic pump in dependence on the identified type of connecting part.

5. The device according to claim 1, wherein the connecting part is a disposable part which is designed for one-off use.

6. The device according to claim 5, wherein the connecting part is produced substantially completely from injection moulded parts.

7. The device according to claim 1, wherein the pump head is coupled to the drive via at least one freewheel when the connecting part is connected as intended to the drive unit.

8. The device according to claim 1, wherein the drive unit additionally comprises a vacuum pump, which serves for suctioning the bodily fluids.

9. The device according to claim 8, wherein the drive unit comprises a housing in which both the drive and the vacuum pump are arranged.

10. The device according to claim 8, wherein the drive which serves for driving the peristaltic pump also serves for driving the vacuum pump.

11. The device according to claim 8, wherein the vacuum pump is a diaphragm pump.

12. The device according to claim 1, wherein the gearing unit is a planetary gearing unit.

13. A device for suctioning bodily fluids and for supplying a fluid substance to a human or animal body, comprising:
    a drive unit having a drive,
    a pump head which is drivable by the drive and
    a connecting part which is releasably connectable to the drive unit having a tube guide which is realized in such a manner for receiving a tube that the tube, when the connecting part is connected as intended to the drive unit, in combination with the pump head, forms a peristaltic pump by way of which the fluid substance is conveyable through the tube to the human or animal body,
    wherein the connecting part is a fluid-collecting container for collecting the suctioned bodily fluids or part of such a fluid-collecting container or an intermediate part for arrangement between the drive unit and such a fluid-collecting container,
    and wherein the connecting part comprises a gearing unit via which the pump head is coupled to the drive when the connecting part is connected as intended to the drive unit.

14. The device according to claim 13, wherein the gearing unit is a planetary gearing unit.

* * * * *